United States Patent [19]

Ross

[11] Patent Number: 4,886,456

[45] Date of Patent: * Dec. 12, 1989

[54] METHODS FOR FORMING DENTAL PROSTHESIS

[75] Inventor: Stanley E. Ross, Boca Raton, Fla.

[73] Assignee: Ross Systems Corporation, Palm Beach, Fla.

[ * ] Notice: The portion of the term of this patent subsequent to May 17, 2005 has been disclaimed.

[21] Appl. No.: 192,128

[22] Filed: May 10, 1988

Related U.S. Application Data

[62] Division of Ser. No. 920,781, Oct. 20, 1986, Pat. No. 4,744,753.

[51] Int. Cl.$^4$ ............................................. A61C 8/00
[52] U.S. Cl. .................................... 433/173; 433/214
[58] Field of Search ............... 433/173, 174, 175, 176, 433/193, 195, 201.1, 210, 213, 214, 220, 221, 223; 264/16, 19

[56] References Cited

U.S. PATENT DOCUMENTS

| | | | |
|---|---|---|---|
| 711,324 | 10/1902 | Lacy | 433/173 |
| 866,304 | 9/1907 | Roach | 433/177 |
| 984,782 | 2/1911 | Starr | 433/213 |
| 2,210,424 | 8/1940 | Morrison | 433/175 |
| 2,318,402 | 5/1943 | Karlstrom | 433/213 |
| 2,721,387 | 10/1955 | Ashuckian | 433/173 |
| 3,023,500 | 3/1962 | Prosen | 433/213 |
| 3,286,350 | 11/1966 | Cooper | 433/74 |
| 3,729,825 | 5/1973 | Linkow et al. | 433/176 |
| 3,755,897 | 9/1973 | Kurer | 433/213 |
| 3,797,113 | 3/1974 | Brainin | 433/173 |
| 3,934,347 | 1/1976 | Lash et al. | 433/173 |
| 4,180,910 | 1/1980 | Straumann et al. | 433/173 |
| 4,205,443 | 6/1980 | Weissman | 433/74 |
| 4,253,835 | 3/1981 | Ware | 264/16 |
| 4,359,318 | 11/1982 | Gittleman | 433/173 |
| 4,431,416 | 2/1984 | Niznick | 433/174 |
| 4,439,152 | 3/1984 | Small | 433/173 |
| 4,443,192 | 4/1984 | Blitz | 433/74 |
| 4,488,875 | 12/1984 | Niznick | 433/173 |
| 4,531,915 | 7/1985 | Tatum, Jr. | 433/173 |

FOREIGN PATENT DOCUMENTS 1291470 10/1972 United Kingdom .
1352188 5/1974 United Kingdom .

OTHER PUBLICATIONS

"A 15-Year Study of Osseointegrated Implants in the Treatment of the Edentulous Jaw", Adell et al, 1981, vol. 10, pp. 387–416.
Brochure, by Metaux Precieux SA Metalor, Switzerland publication date (unknown) Identified as "J01", 3 pages.
Brochure, by Metaux Precieux SA Metalor, Switzerland publication date (unknown) Identified as "J11", 4 pages.
Brochure, "The Interpore IMZ Osteointegrated Implant System", Rev. 1, 1986 by Interpore International, pp. Title to 24.

Primary Examiner—John J. Wilson
Attorney, Agent, or Firm—Burns, Doane, Swecker & Mathis

[57] ABSTRACT

A dental prosthesis is formed by attaching an internally threaded sleeve to a post by means of a heat-meltable material. A dimensionally stable, heat-meltable material is applied to the post and around the sleeve. The heat-meltable materials are melted and replaced by a permanent material. A screw is inserted into the sleeve prior to the melting step. The melting and replacing steps comprise steps in an investment-type casting procedure wherein a unit comprised of the post, the sleeve, the screw, and the heat-meltable materials is embedded in an investment material such that a head of the screw is embedded in the investment material to maintain the positional relationship of the sleeve relative to the post during the melting step. A release material is applied over a body defined by the permanent material. A dimensionally stable, heat-meltable material is applied over the release material and is melted and replaced with a permanent material which forms an overlay capable of being removed upon removal of the screw.

2 Claims, 4 Drawing Sheets

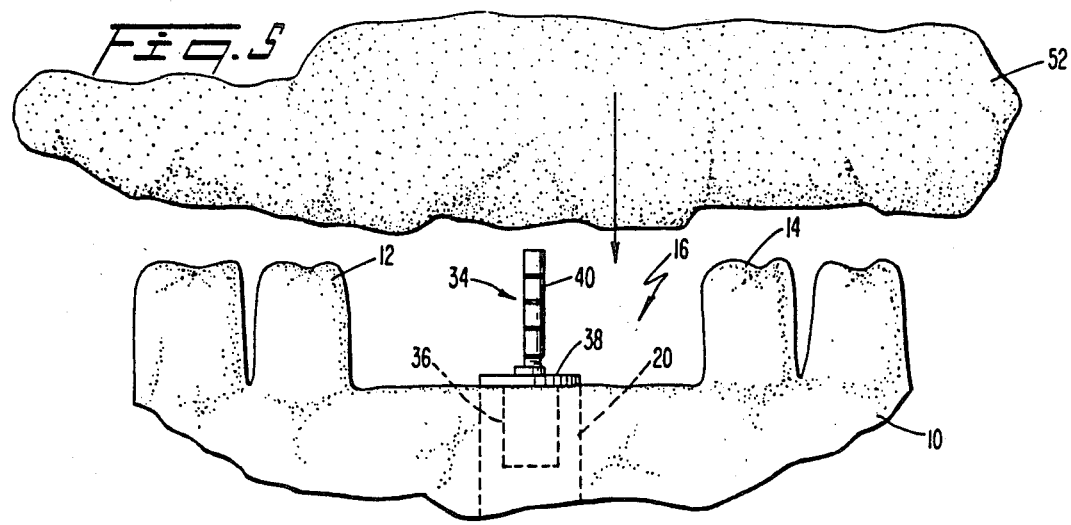
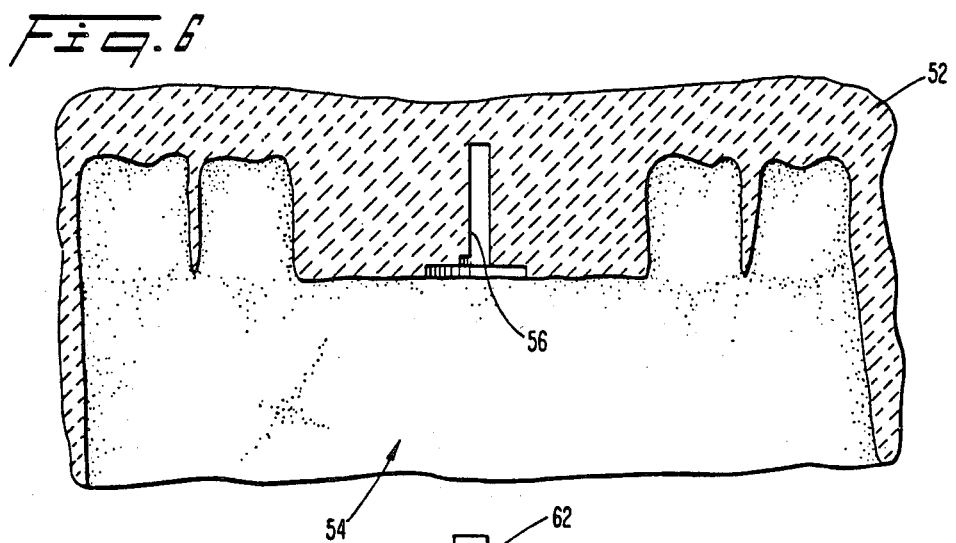
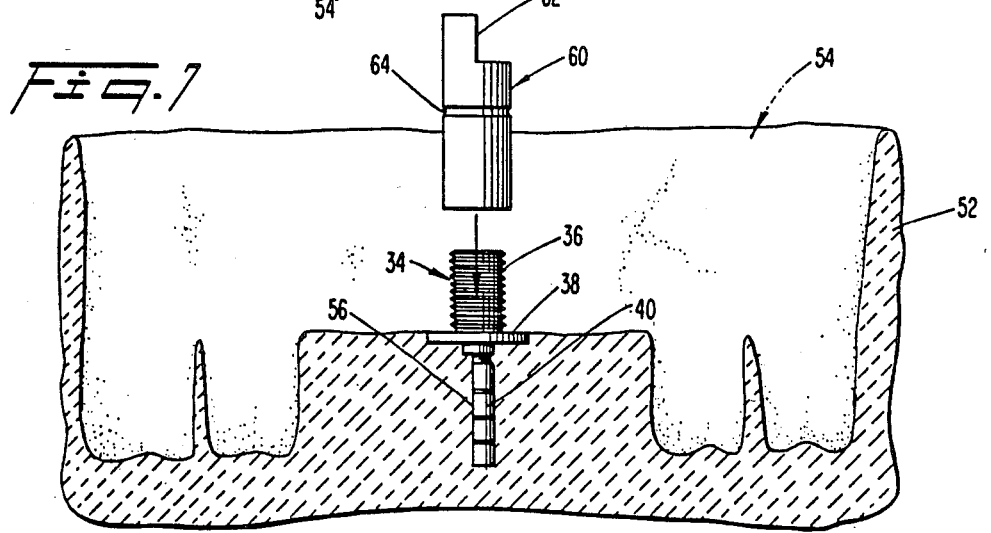

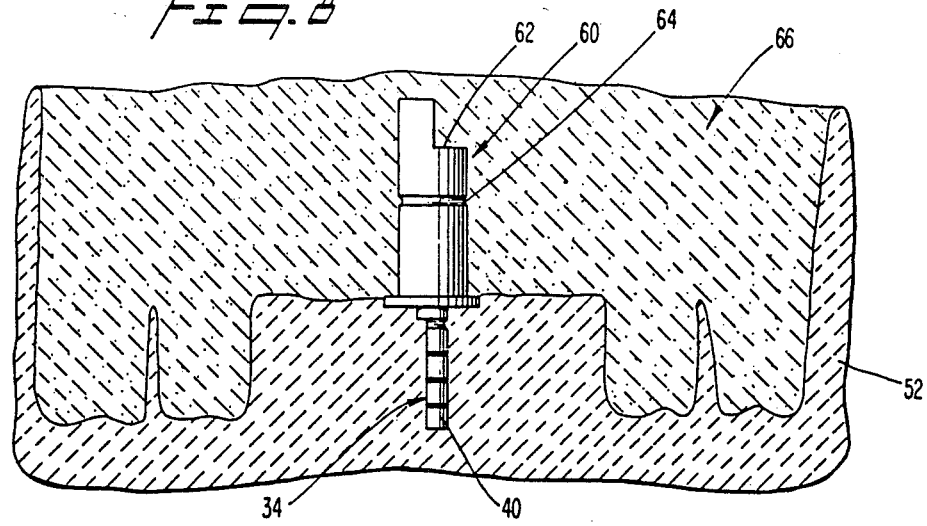
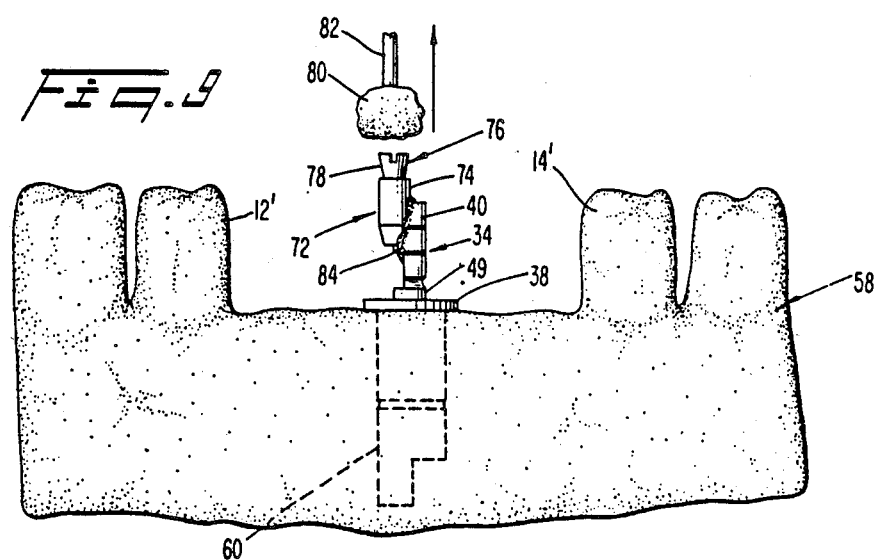
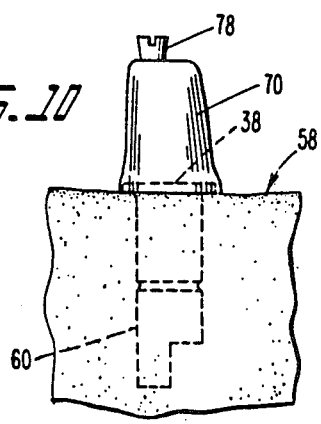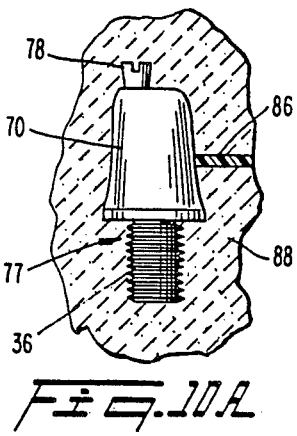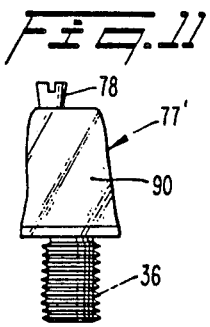

METHODS FOR FORMING DENTAL PROSTHESIS

This application is a divisional of application Ser. No. 920,781, filed Oct. 20, 1986, now U.S. Pat. No. 4,744,753.

RELATED INVENTIONS

This invention is related to the invention disclosed in commonly assigned U.S. Pat. Nos. 4,744,754, 4,744,755, and 4,744,576, issued May 17, 1988, respectively, by the present inventor.

BACKGROUND AND OBJECTS OF THE INVENTION

The present invention relates to the forming of dental prostheses and attaching same to the jaw of a patient.

There have been previously proposed numerous techniques for forming dental prostheses and attaching same to a patient's jaw. For example, in U.S. Pat. No. 4,431,416 it is disclosed to affix a self-tapping threaded anchor within a patient's jaw bone such that a recess in the anchor opens into the patient's mouth. A pillar is then cemented into the recess such that a snap socket on the end of the pillar is adapted to receive a mating part of the prosthesis. The pillar can be bent in order to achieve a certain degree of parallelism relative to the adjacent teeth. However, the bending of the pillar may result in a cracking of the pillar, and, thus, the extent to which the pillar can be bent is limited. If proper parallelism and jaw-to-jaw height are not achieved, the teeth will not correctly occlude. Furthermore, unless the prosthesis has an easily replaceable crown, the prosthesis cannot be easily repaired in the event of damage or wear thereof.

In lieu of inserting a bendable pillar into the anchor, a plastic pillar could be inserted into the anchor which is then cut and shaped while in the patient's mouth in an attempt to achieve parallelism with adjacent teeth. However, the equipment necessary to achieve a precise degree of parallelism will not fit into a patient's mouth and thus the chances of achieving exact parallelism are reduced. After being shaped, the pillar could be inserted into a conventional investment-type casting apparatus which melts the plastic and replaces it with a permanent material such as gold.

A brochure presented by Metaux Precieux SA Metalor, describes steps for fabricating a prosthesis which is to be inserted into a tooth cavity. Wax is inserted into the tooth cavity to form a wax model. The wax model is removed from the tooth cavity, and an internally threaded sleeve is pushed directly into the wax body. Then, the sleeve is removed from the wax body and is replaced by a positioner which occupies the hole made by the sleeve. The wax body is then subjected to a conventional investment-type casting procedure wherein the wax is melted-out and replaced by a permanent material such as gold. Then, the positioner is removed and replaced by the sleeve which is soldered in place within the gold body. A screw is threaded into the sleeve and a release material is applied to the gold body followed by the application of a wax layer which conforms to the desired tooth shape. Following an investment-type casting operation, the wax is replaced by a material such as gold to form a crown or overlay which is removable from the original gold body, due to the release material. The original gold body is cemented into the tooth cavity, and the overlay is able to be replaced by removal of the screw. This procedure is very time-consuming due especially to the need for soldering the sleeve into the gold body. Also, the pushing of the sleeve into the wax body can deform the wax body from its intended shape. The overall procedure is not well suited to the creation of a prosthetic tooth to be installed in an anchor attached within a patient's jaw.

A procedure for forming a dental prosthesis to be mounted in an anchor has been proposed by Interpore International of Irvine, Calif. That procedure involves the implanting of an anchor in a patient's jaw, the anchor having a threaded hole which opens into the interior of the patient's mouth. Into that hole is inserted a threaded stem of a plastic impression pin such that a post of the pin projects beyond the jaw and into the mouth. A clay impression of the dental arch is then made. The impression pin is then unscrewed from the anchor and the post is inserted into the respective cavity of the impression, leaving the threaded stem exposed. A dowel is threaded onto the stem, and a dental model is formed by pouring dental stone into the impression. The dowel becomes permanently embedded within the model. The impression pin is then unscrewed from the dowel and replaced by a titanium element (i.e., a so-called IME). The IME includes an internally threaded hole and an externally threaded stem which is to be threaded into the dowel (and eventually into the anchor once a prosthesis has been formed on the IME). A titanium coronal screw is threaded into the internally threaded hole so as to project a predetermined distance out of the hole. A sleeve is applied around the screw and is waxed-up so as to form a shaped wax body. The unit is then subjected to a conventional investment-type casting step wherein the wax is replaced by a suitable permanent material such as gold. That gold body can be removed from the IME by removing the screw. A suitable porcelain layer can be baked onto the gold body. With such a procedure, it is very difficult to achieve proper parallelism between the prosthesis and the adjacent teeth, as well as a precise jaw-to-jaw height, because of the inability to bend or cut the screw. As a result, the permanent material is mounted so as to be movable relative to the screw in an attempt to enable the permanent material to "float" and become self-aligned with the opposing teeth of the other jaw.

Another method for forming and installing a dental prosthesis is described in an article by R. Adell et al entitled "A 15-year Study of Osseointegrated Implants in the Treatment of the Edentulous Jaw", printed in the International Journal of Oral Surgery, 1981, Vol. 10, pp. 387–416. As described in that article, a partially self-tapping anchor is threaded into a predrilled, partially pretapped hole in patient's jaw. The anchor includes a threaded hole opening into the patient's mouth. After the healing process, an enlarged abutment is attached to the anchor by means of a first screw which passes through the abutment and enters the threaded hole of the anchor. A bridge is prepared in conventional fashion and is attached to the abutment by means of a second screw which passes through the bridge and enters a threaded hole in the head of the first screw. With such a procedure it is difficult to achieve a proper parallelism between the teeth of the bridge and adjacent teeth, as well as proper jaw-to-jaw height. Moreover, since the bridge rests upon the abutment, gaps are created between the bridge and the gum which are undesirable from an esthetics and phonetics standpoint.

It would be desirable to minimize or obviate the problems of the type discussed above and to advance the science of dental prosthetics.

SUMMARY OF THE INVENTION

In accordance with the present invention, a dental prosthesis is formed by attaching an internally threaded sleeve to a post. A dimensionally stable, heat meltable material is applied to the post and around the sleeve. The heat-meltable material is melted and replaced by a permanent material.

Preferably, a screw is inserted into the sleeve prior to the melting step. The melting and replacing steps comprise steps in an investment-type casting procedure wherein a unit comprised of the post, the sleeve, the screw, and the heat-meltable materials is embedded in an investment material such that a head of the screw is embedded in the investment material to maintain the positional relationship of the sleeve relative to the post during the melting step.

Preferably, a layer of dimensionally stable, heat-meltable material is applied over the body in the shape of an overlay. The layer is removed from the body and is melted and replaced with a permanent material which forms an overlay capable of being removably attached to the body by the screw. A release material can be applied to the body before the heat-meltable material is applied thereto.

The post preferably comprises a portion of a pin which includes a flange and an externally threaded stem. The post projects from one side of the flange, and the stem projects from an opposite side of the flange. The dimensionally stable, heat-meltable material is applied upon said one side of the flange during the applying step. The stem is adapted to be threaded into a threaded hole of a jaw anchor.

To install the prosthesis, it is preferable to drill a bore in a patient's jaw bone. An anchor is inserted into the bore, the anchor including an internally threaded opening accessible from within the patient's mouth. An externally threaded stem of the pin is inserted into the threaded opening. The pin includes a flange having a first side from which the stem projects, and a second side from which a post extends in a direction opposite the stem, such that the flange seats upon the anchor and the post projects away from the anchor. The pin has a non-symmetrical, non-circular cross-sectional shape. There is then formed an impression of at least a portion of the patient's jaw including the post, such that the post forms a recess in the impression. The pin is removed from the anchor and the post is inserted into the recess of the impression, such that the threaded stem extends away from the impression. A hardenable substance is poured into the impression to form a dental model in which the stem is disposed. A fastener assembly is attached to the post, the fastener assembly comprising an internally threaded sleeve and a screw threaded therein. Formed upon the flange and around the post and sleeve is a shaped mass of dimensionally stable, heat-meltable material. That material is melted and replaced with a permanent material, and a layer of dimensionally stable heat-meltable material is applied over the release material. The layer of heat-meltable material is removed from the body and then is melted and replaced with a permanent material which forms an overlay capable of being removably attached to the body by the screw.

BRIEF DESCRIPTION OF THE DRAWING

The objects and advantages of the invention will become apparent from the following detailed description of a preferred embodiment thereof in connection with the accompanying drawings, in which like numerals designate like elements, and in which:

FIG. 5 is an elevational view of a portion of a dental arch with the pin installed therein, as a piece of clay or dental impression material is being pressed onto the arch;

FIG. 6 is a view of the clay after an impression has been made and the clay has been removed from the dental arch;

FIG. 7 is a view of the clay impression after it has been inverted and the pin has been reinserted therein, and a protective sheath is in the process of being installed onto a threaded stem portion of the pin;

FIG. 8 is a view similar to FIG. 7 after the sheath has been installed and plaster has been poured into the clay impression;

FIG. 9 is an elevational view of the plaster model just after a fastener assembly has been attached to a post portion of the pin;

FIG. 10 is an elevational view of the pin, still mounted in the plaster model, after the pin has been waxed-up;

FIG. 10A is a view of a preliminary unit comprising the pin, the fastener assembly, and the wax, disposed in an investment material prior to carrying out an investment-type casting operation;

FIG. 11 is an elevational view of the unit after the investment-type casting operation wherein the wax has been replaced by a permanent material to form a secondary unit;

DETAILED DESCRIPTION OF A PREFERRED EMBODIMENT OF THE INVENTION

Depicted in FIG. 5 is a portion of the dental arch of a lower jaw 10 in a human mouth. Disposed between two healthy teeth 12, 14 is a gap 16 in which a dental prosthesis is to be placed in accordance with the present invention, the steps of which will first be summarized and then described in greater detail.

Figure 1:
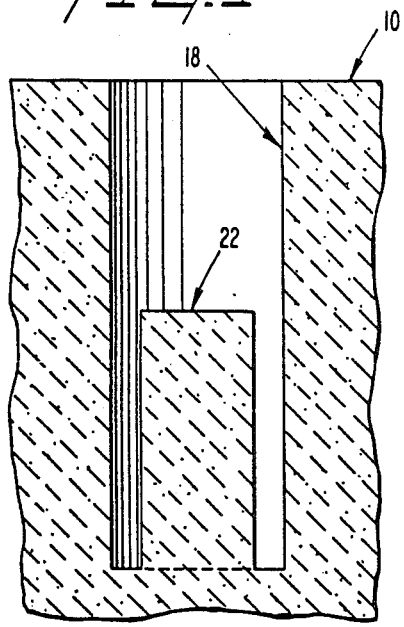
FIG. 1 is a vertical sectional view taken through a bore formed in a jaw bone of a patient.
Figure 2:
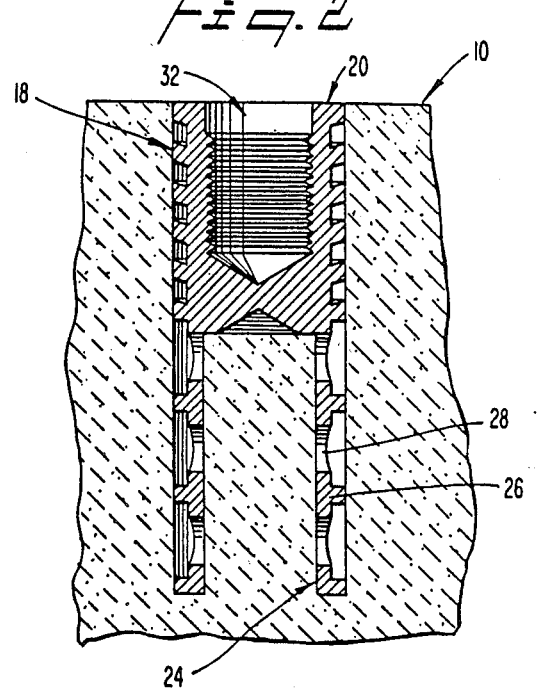
FIG. 2 is a view similar to FIG. 1 after an anchor has been pushed into the bore.

A hole 18 is drilled in a portion of the jaw bone disposed within the gap 16 as depicted in FIG. 1, and an implant or anchor 20 is inserted into the hole (FIG. 2).

Figure 3:
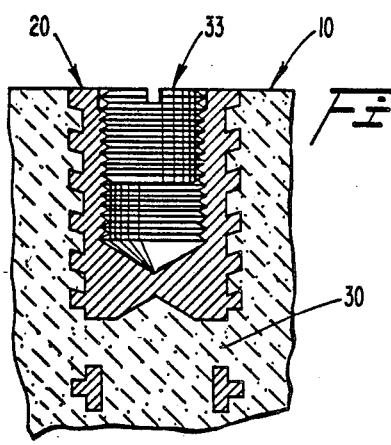
FIG. 3 is a view similar to FIG. 2 after a healing screw has been inserted into the anchor, and the bone tissue has grown through openings in the anchor.
Figure 4:
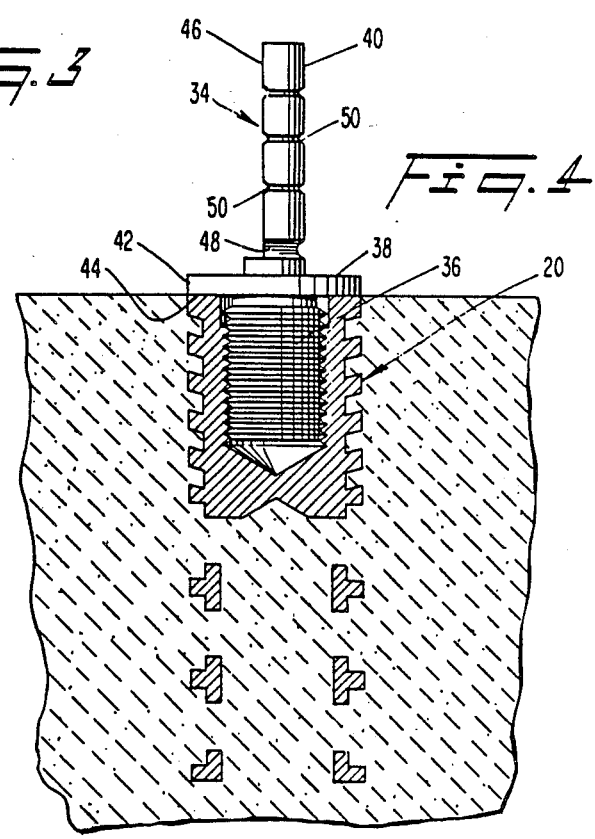
FIG. 4 is a view similar to FIG. 2 after the healing screw has been removed and a pin according to the present invention has been threaded into the anchor.

A healing screw 33 (FIG. 3) is threaded into a threaded hole 32 of the anchor during the healing period wherein the anchor becomes permanently affixed to the jaw bone tissue. Then the healing screw is removed and replaced by a pin 34 such that a post portion 40 of the pin projects beyond the jaw (FIG. 4). A clay impression 52 of the dental arch (including the post) is taken (FIGS. 5 and 6), whereafter the pin 34 is unscrewed from the anchor 20. A transgingival screw (not shown) is screwed into the anchor hole 32 to prevent gum tissue from growing into that hole while a prosthesis is being prepared. The post 40 of the pin is inserted into the corresponding hole 56 of the clay impression, and a protective sheath 60 is threaded onto the exposed threaded stem 36 of the post (FIG. 7). Then, a dental model 58 is formed from the impression (FIGS. 8 and 9), with the sheath 60 becoming embedded therein.

The post 40 is then cut to achieve a desired degree of parallelism with the adjacent teeth and occlusion with the opposing teeth (FIG. 9). A fastener assembly 72 is attached to the post (FIG. 9), and dental wax 70 is applied to the post 40 to form a body shaped and oriented compatibly with the shape and orientation of the adjacent teeth 12′, 14′ (FIG. 10). In so doing, the sleeve 74 of the fastener assembly 72 becomes embedded in the wax 70.

The unit 77 comprised of the pin 34, the wax body 70, and the fastener assembly 72, is then removed from the dental model and subjected to a conventional investment-type casting operation (FIG. 10A) wherein the wax is melted and replaced by a permanent material, such as gold, in which the sleeve 74 becomes encased (FIG. 11). A layer of release material 94 is applied to the gold body 90 and a wax layer 96 is applied thereover which is shaped in conformance with the desired overlay shape. In a subsequent investment-type casting operation, the wax is replaced by a permanent material such as gold which forms an overlay 92 that can be removed from the gold body upon removal of the screw 76.

A more detailed explanation of the invention will now be provided.

The anchor 20 may be of the type described in the afore-mentioned U.S. Pat. Nos. 4,744,755 and 4,744,754 and installed in the manner described therein. Briefly, the hole 18 is drilled in the jaw bone by means of a trephine drill which leaves a cylindrical center core of bone 22. The anchor 20 is pushed longitudinally into the hole such that the core 22 enters a front recess 24 of the anchor (FIG. 2). The anchor side wall 26 includes throughholes 28 through which bone tissue 30 grows (FIG. 3). The anchor thus becomes affixed within the jaw absent the use of cement. A rear end of the anchor 20 includes a threaded hole 32 which opens into the patient's mouth. That hole is adapted to receive a healing screw 33 (FIG. 3) which is inserted into the hole 32 prior to the installation of the anchor into the hole 18 and remains in the hole 32 during the healing process. Thereafter, the screw 33 is replaced by the pin 34.

The stem 36 of the pin 34 projects from one side of a circular flange 38, and the post 40 projects from the other side of the flange 38. The stem and post are both of smaller width (cross-section) than the flange as is evident from FIG. 7. The outer diameter of the flange corresponds to the outer diameter of the anchor. Hence, the outer edge 42 of the flange will lie flush with the outer edge 44 of the anchor 20 to avoid the creation of a space between those members into which food and bacteria could enter. The pin is preferably formed of a biocompatible material such as a titanium alloy or commercially pure titanium.

Figure 4A:
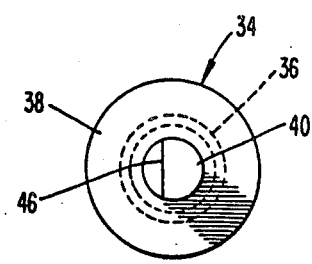
FIG. 4A is a longitudinal end view of the pin depicted in FIG. 4.
Figure 12:
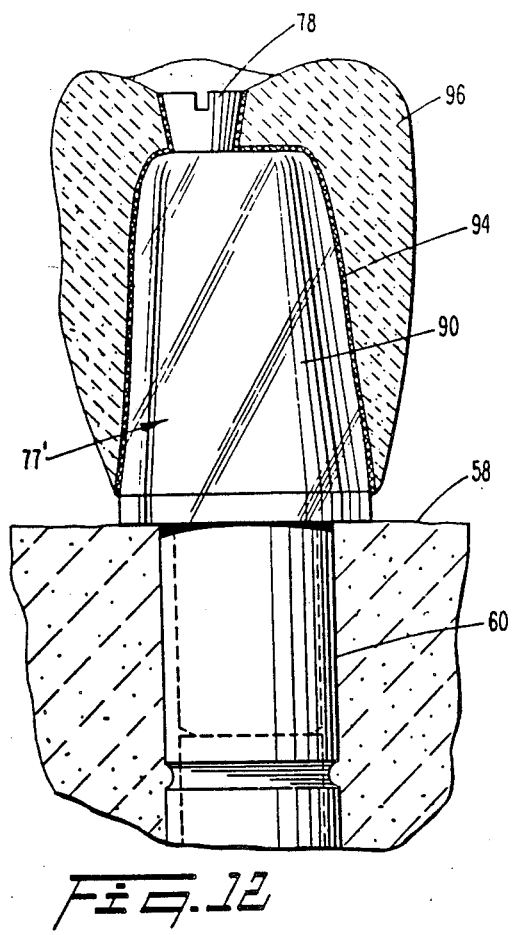
FIG. 12 is an elevational view of the secondary unit mounted in the plaster model, with layers of release material and wax disposed on the body of permanent material.
Figure 13:
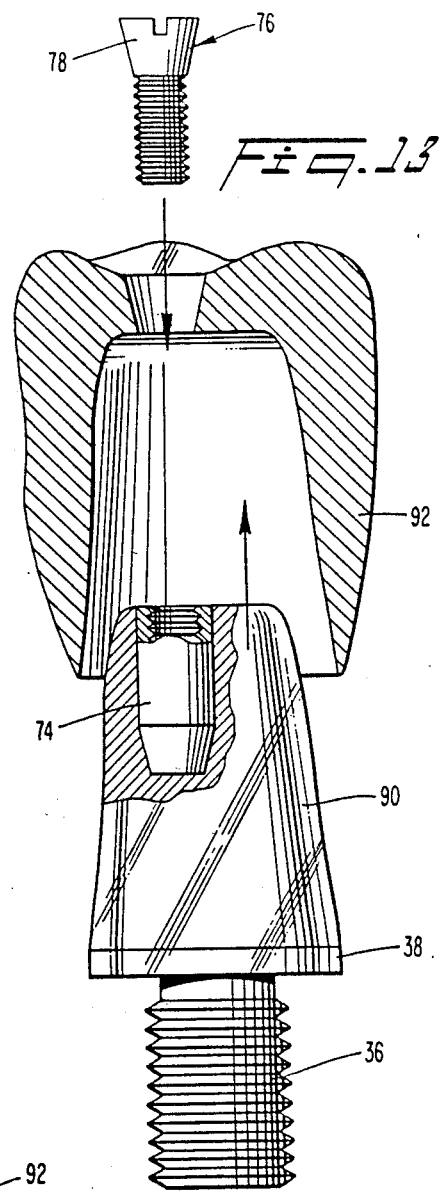
FIG. 13 is an exploded view of the secondary unit and an overlay, with a screw of the fastener assembly in a removed condition.

The post 40 is of non-symmetrical cross-sectional shape (FIG. 4A) due to a flat portion 46 of the post which terminates just above the flange 38. A circumferential groove 48 is formed in the post at a slight distance above the flange 38 (FIG. 4). The outer periphery of the post is of longitudinally irregular shape due to the presence of that groove 48 plus a series of additional circumferential grooves 50, which are spaced apart in the longitudinal direction of the post.

The stem 36 can be screwed into the anchor by hand, or by a tool, if desired. Once the pin 34 has been tightly threaded in place, an impression 54 of the dental arch (including the post 40) is made in a conventional manner such as by pressing a piece of clay 52 over the dental arch (FIGS. 5, 6). The impression 54, which includes a cavity 56 of non-circular cross-section formed by the post 40, serves as a mold to create a plaster dental model 58 (FIG. 9) of the arch in a conventional manner. Prior to forming the dental model, the pin 34 is unscrewed from the anchor 20 and replaced with a transgingival screw (not shown) which is screwed into the anchor hole 32. The transgingival screw includes a head which projects beyond the gum line to prevent the gum from growing over the anchor. After being removed from the anchor, the post 40 is inserted into the cavity 56 as depicted in FIG. 7. Due to the non-symmetrical cross-sectional shape of the cavity 56, the position of the post 40, once inserted into the cavity 56, will correspond precisely to the position of the post in the jaw when the impression was made. Hence, when the dental model is made, the orientation of the post relative to the adjacent teeth 12′, 14′ of the model 58 will correspond precisely to the orientation of the post 40 relative to the actual teeth 12, 14 of the patient.

It is desirable to protect the screw thread of the stem 36 during the formation of the dental model. Accordingly, a sheath 60 (FIG. 7) is positioned over the stem 36 before the model is formed. The sheath 60 is of generally cylindrical configuration and includes a threaded recess at one end and a cut-out 62 or step at the opposite end. A circumferential groove 64 is provided in the outer surface of the sheath 60. The threaded recess of the sheath is screwed onto the threaded stem 36 of the pin 34, and then the dental model 58 is formed by pouring plaster or dental stone 66 into the clay impression in a conventional manner (FIG. 8). Accordingly, the sheath 60 becomes embedded in the dental model (FIG. 9). Rotation of the sheath 60 within the dental model is prevented due to the non-circular cross-section defined by the step 62, and longitudinal dislodgement of the sheath 60 from the model 58 is prevented due to the longitudinally irregular periphery defined by the groove 64 in the sheath.

As a result, the operator possesses an identical model 58 of the patient's dental arch (FIG. 9), with the pin 34 removably threaded in the model. The operator is then able to form the post 40 with a shape that is compatible in size and orientation to the adjacent teeth 12′, 14′, and with a height that is compatible with the jaw-to-jaw height. This forming operation is accomplished by suitably cutting the post 40 and applying to the post a heat-meltable substance capable of being worked and shaped, such as dimensionally stable dental wax 70. The cutting and waxing of the post is performed while the pin 34 is mounted in the dental model 58. As a result, the shaping of the pin to gain parallelism can be achieved without discomfort to the patient and with superior accuracy, since the shaping can be performed with precision tools and guides which cannot be employed within the confines of a patient's mouth. It is important to note that since the cavity 56 defined in the clay 52 by the post 40 was of non-symmetrical cross-sectional shape, the post could be inserted back into that cavity in only one possible position, i.e., a position corresponding to its position within the anchor 20. Thus, the position of the post relative to the adjacent teeth 12', 14' within the model 58 will correspond precisely to the position of the post 40 relative to the teeth 12, 14 when the pin is eventually screwed into the anchor 20. Therefore, the parallelism achieved by the post and wax body relative to the model teeth 12', 14' will be carried forward relative to the teeth 12, 14 when the pin is eventually screwed back into the anchor 20.

Prior to the waxing step, the fastener assembly 72 is attached to the post 40. The fastener assembly comprises the threaded sleeve 74 and the screw 76, both formed of a suitably heat-resistant alloy. The sleeve 74 contains internal threads for threadedly receiving the screw 76. The head 78 of the screw is adhered to a piece of sticky wax 80 carried at the end of a manually held rod 82 to enable the fastener assembly 72 to be manually located at a desired location relative to the post 40. Then the sleeve 74 is adhered to the post 40 by a bit of heat-meltable wax 84 which quickly hardens to enable the piece of sticky wax 80 to be removed, leaving the fastener assembly 72 adhered to the post 40 (FIG. 9). The fastener assembly 72 can be oriented parallel to the post, or at an angle relative thereto; the assembly 72 can be disposed vertically or horizontally if desired.

The dimensionally stable dental wax 70 is then applied to the post to create a shaped body (FIG. 10) which is compatible in shape and orientation to the adjacent teeth. The wax is applied so as to encase the sleeve 74 while leaving the head 78 of the screw 76 exposed. The flange 38 of the pin 34 serves as a shelf upon which the wax 70 is applied.

The preliminary unit 77 comprising the pin 34, the shaped wax body 70, and the fastener assembly 72 is unscrewed from the dental model, i.e., unscrewed from the sheath 60. This can be performed by a pliers-like tool which engages the outer edge 42 of the flange to avoid damaging or deforming the wax body 70. The unit is then placed in a conventional investment-type dental casting material and machine which replaces the wax 70 with a permanent material such as gold, porcelain, acrylic, etc. The nature of that casting process is well known in the art and can be summarized as follows. The wax body is attached to a sprue 86 formed of a meltable material such as plastic. The entire unit and sprue are encased in a conventional pliable investing material 88 (FIG. 10A) which is pressed against the outer periphery of the unit 77. A conventional investment material can be used, such as that available from Whip-Mix Corp. of Louisville, Ky., under the name Beauty Cast. Thereafter, the invested unit 77 is subjected to sufficient heat to melt the wax 70, 84 and the sprue 86. When this melting occurs, the fastener assembly 72 is held in place relative to the post 40 since the head 78 of the screw is embedded in the investment material (FIG. 10A). Then, under the influence of centrifugal force, the melt is discharged and replaced by a liquified permanent material, such as melted gold, which occupies the void created by the discharged melt. Upon hardening of the gold, the unit 77' appears identical to its previous appearance except that the wax body 70 has been replaced by gold 90 (FIG. 11). The unit 77' thus forms a secondary unit for receiving the overlay or crown. The sleeve 74 may be provided with projections (not shown) to enhance its securement within the gold body 90.

Next to be formed is the overlay 92 which is to be removably attachable to the secondary unit 77'. The overlay 92 is formed by applying a conventional release or parting material 94 to the outer periphery of the gold body 90 and the head 78 of the screw 76, and then forming a layer 96 of dimensionally stable wax over the parting material. These steps are performed after the secondary unit 77' has been screwed back into the sheath 60 of the dental model 58. The wax layer 96 is shaped in accordance with the desired shape of the overlay 92. The wax layer 96 and screw 76 are removed from the body 90, and the screw is reinserted into the wax layer 96. The assembly of the layer 96 and screw 76 is inserted into an investment-type casting material and machine, whereupon the wax layer 96 is replaced with a permanent material such as gold, porcelain or acrylic for example, by means of an investment-type casting operation, to form the overlay 92. Due to the presence of the parting material, the overlay does not adhere to the head of the screw. The overlay can be placed upon the body 90 and attached thereto by the screw 76. Thus, if the overlay 92 becomes damaged or worn, it can be easily replaced. If the overlay 92 is formed of gold, a porcelain coating can be formed thereon by a conventional baking process. The insert comprised of the unit 77' is attached to the anchor 20 by screwing the stem 36 into the threaded hole 32 of the anchor 20. Then, the overlay 96 is attached by the screw 76. The prosthesis assumes the same degree of parallelism in the patient's mouth as was achieved in the dental model since, upon screwing the pin in place, the pin is rotated to the same rotational position as when screwed into the model.

Figure 14:
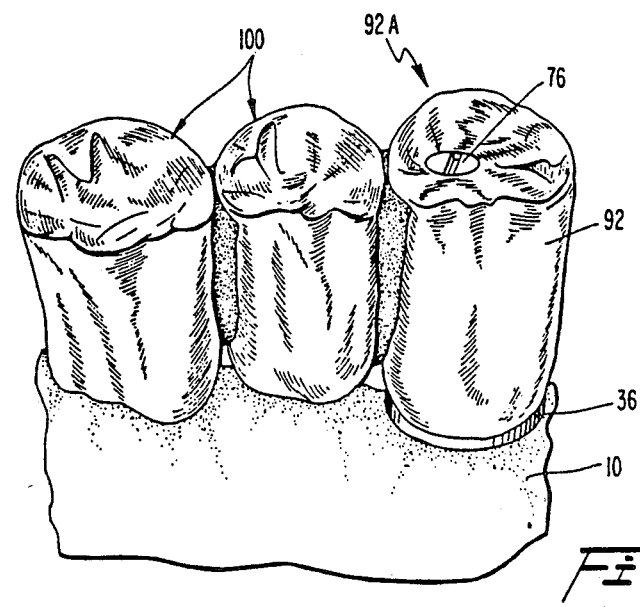
FIG. 14 is a perspective view of a bridge attached to a jaw bone in accordance with the present invention.

The flange 38 abuts flush against the end of the anchor. Since the flange is formed of a biocompatible material, the gum tissue will be able to grow into engagement with the edge 42 of the flange and thereby hide the flange from view. The overlay may comprise a single tooth, or a bridge 92A (FIG. 14) comprised of a plurality of teeth. If a bridge 92A is to be formed, then in addition to the wax layer 96 applied to the parting material 94, one or more additional wax bodies (not shown) are formed which are interconnected at their sides and one of which being connected to the wax layer 96. That entire assembly is then cast to form a bridge 92A comprising the portion 92 attached to the secondary unit, and one or more adjacent teeth 100 attached to the portion 92.

In accordance with the present invention there is provided a novel method of forming a dental prosthesis. The use of a base member in the form of a pin comprised of a threaded stem, a flange, and a post provides significant advantages. The post is capable of being cut and shaped while disposed within a dental model and provides a rigid structure onto which the dental wax can be applied. Thus, the task of forming a prosthesis which conforms to the shape and orientation of the adjacent teeth and the jaw-to-jaw height is greatly facilitated. The flange itself forms a shelf upon which the dental wax can be supported. The threaded stem enables the pin to be inserted into the anchor without the use of cement. In fact, the present system completely avoids the use of cement, thereby eliminating the risk for biodegradation to occur which would create voids into which food and bacteria could enter.

The present invention makes it simple to achieve precise parallelism between the prosthetic tooth (or teeth) and the adjacent teeth in all directions. This parallelism can be made with precision since the post 40 is shaped outside of the mouth and, thus, shaping tools and guides can be employed which could not be utilized within the confines of the patient's mouth. Even though the shaping of the pin is achieved outside of the mouth, the pin is shaped while oriented in the same position relative to the adjacent teeth as when the pin is eventually replaced into the anchor. This is due to the non-symmetrical cross-sectional shape of the post which forms a corresponding cavity in the clay impression material, thereby assuring that precise registration of the pin occurs in the clay impression and plaster model. Since the height of the pin can be shortened, precise jaw-to-jaw height can be achieved. Therefore, the teeth can be made to occlude (bite) properly.

The post itself is shaped to achieve a positive and reliable attachment to the gold body. That is, relative movement between the gold body and post is prevented by the non-circular cross-section and irregular longitudinal profile of the post.

The flange is circular and engages a circular end of the anchor. The flange is of the same diameter as that circular end of the anchor to avoid the presence of voids into which food and bacteria can enter. Also, the prosthesis will present a more pleasing appearance. The absence of gaps between the prosthesis and gums prevents the occurrence of problems with the patient's phonetics.

The incorporation of the fastener assembly within the prosthesis is achieved simultaneously with a casting step; no subsequent cementing or soldering is required. This is made possible by maintaining the screw in position by means of the investment material during the initial casting step to maintain the sleeve in a fixed position even after the wax has been melted. Furthermore, the pin is waxed-up around the sleeve, rather than pushing the sleeve into the wax. Thus, the wax body will not be deformed.

Since the crown portion is removable, due to the presence of the removable screw, the prosthesis can be easily repaired when damaged or worn.

By forming the pin of commercially pure titanium, a high degree of biocompatibility with the gum tissue exists, promoting the chances for a seal or hemi-dessmissomal adaptation of gum tissue to be created above the anchor.

It will be appreciated that the fastener assembly can be disposed in virtually any location and orientation so as to be adapted to all types of repair and restorations from an aesthetics standpoint.

Attention is also directed to the fact that the present invention makes it possible to form the base and overlay outside of the patient's mouth, thereby minimizing discomfort to the patient.

Although the present invention has been described in connection with a preferred embodiment thereof, it will be appreciated by those skilled in the art that additions, modifications, substitutions, and deletions not specifically described, may be made without departing from the spirit and scope of the invention as defined in the appended claims.

What I claim is:

1. A method of forming a dental prosthesis, comprising the steps of:

drilling a bore in a patient's jaw bone, inserting into said bore an anchor formed of a material which is biocompatible with bone tissue, said anchor being apertured at a front end thereof and including an internally threaded opening at a rear end thereof which is accessible from within the patient's mouth, inserting into said threaded opening an externally threaded stem of a pin, said pin including a post extending in a direction opposite said stem, said post being of non-symmetrical, non-circular cross-section, forming an impression of at least a portion of said jaw including said post, such that said post forms in said impression a cavity of non-symmetrical, non-circular cross-section, removing said pin from said anchor and inserting said post into said cavity such that said threaded stem extends away from said impression, threading a sheath onto said threaded stem, pouring a hardenable substance into said impression to form a dental model in which said sheath is disposed, and such that said post is oriented in said model in the same position as when disposed in said anchor, determining where to cut said post to a desired shape while said post is in said dental model, cutting said post to that desired shape, forming around said cut post a shaped mass of dimensionally stable, heat meltable material to achieve a desired shape thereof while said pin is in said dental model, and melting at least said heat meltable material and replacing same with a permanent material.

2. A method of forming a dental prosthesis comprising the steps of:

providing within a dental model of a portion of a patient's jaw a pin having a flange, an externally threaded stem projecting from one side of said flange, and a post projecting from an opposite side of said flange, said post including a portion of non-circular cross-sectional shape and irregular longitudinal profile, determining where to cut said post to a desired shape while said post is in said dental model, cutting said post to that desired shape thereof, forming upon said flange and around said cut post a shaped mass of dimensionally-stable, heat-meltable material to achieve a desired shape thereof while said pin is in said dental model, removing said pin from said dental model, and melting at least said heat meltable material and replacing same with a permanent material.

* * * * *